(12) United States Patent
Gondek et al.

(10) Patent No.: US 9,149,420 B2
(45) Date of Patent: Oct. 6, 2015

(54) O/W-GEL-COMPOSITIONS HAVING PENTAERYTHRITOL ESTERS OR OLIGOMERS THEREOF

(75) Inventors: Helga Gondek, Duesseldorf (DE); Ulrich Issberner, Ambler, PA (US); Catherine Weichold, Aachen (DE)

(73) Assignee: Cognis IP Management GmbH, Duesseldorf (DE)

(*) Notice: Subject to any disclaimer, the term of this patent is extended or adjusted under 35 U.S.C. 154(b) by 2587 days.

(21) Appl. No.: 11/547,599

(22) PCT Filed: Mar. 26, 2005

(86) PCT No.: PCT/EP2005/003232
§ 371 (c)(1),
(2), (4) Date: Aug. 14, 2007

(87) PCT Pub. No.: WO2005/097055
PCT Pub. Date: Oct. 20, 2005

(65) Prior Publication Data
US 2008/0064761 A1  Mar. 13, 2008

(30) Foreign Application Priority Data
Apr. 5, 2004 (DE) .......................... 10 2004 017 221

(51) Int. Cl.
| | |
|---|---|
| C08F 2/32 | (2006.01) |
| A61K 8/33 | (2006.01) |
| C11D 3/37 | (2006.01) |
| A61K 47/44 | (2006.01) |
| A61K 8/37 | (2006.01) |
| C11D 17/00 | (2006.01) |
| C11D 7/26 | (2006.01) |
| A61Q 19/10 | (2006.01) |
| A61K 8/81 | (2006.01) |
| C11D 1/66 | (2006.01) |

(52) U.S. Cl.
CPC . *A61K 8/33* (2013.01); *A61K 8/375* (2013.01); *A61K 8/8147* (2013.01); *A61K 8/8158* (2013.01); *A61Q 19/10* (2013.01); *C11D 1/667* (2013.01); *C11D 3/3765* (2013.01); *C11D 3/3773* (2013.01); *C11D 7/266* (2013.01); *C11D 17/003* (2013.01)

(58) Field of Classification Search
None
See application file for complete search history.

(56) References Cited

U.S. PATENT DOCUMENTS

| | | | |
|---|---|---|---|
| 1,951,593 A | 3/1934 | Bradley | |
| 2,427,255 A | 9/1947 | Burrell et al. | |
| 2,441,555 A | 5/1948 | Robert et al. | |
| 2,705,722 A | 4/1955 | Barsky | |
| 2,975,152 A | 3/1961 | Hurwitz et al. | |
| 3,976,789 A | 8/1976 | Tomita et al. | |
| 4,113,635 A | 9/1978 | Sakurai et al. | |
| 4,290,337 A | 9/1981 | Kuwata et al. | |
| 4,332,702 A * | 6/1982 | Lindner ..................... 524/178 |
| 4,400,295 A * | 8/1983 | Ootsu et al. .................... 516/56 |
| 5,304,665 A | 4/1994 | Cooper et al. | |
| 5,374,716 A | 12/1994 | Biermann et al. | |
| 5,436,006 A | 7/1995 | Hirose et al. | |
| 5,576,425 A | 11/1996 | Hill et al. | |
| 5,637,291 A * | 6/1997 | Bara et al. ....................... 424/59 |
| 5,741,919 A | 4/1998 | O'Lenick et al. | |
| 6,086,787 A * | 7/2000 | Schambil et al. ............. 424/401 |
| 6,432,419 B2 | 8/2002 | Kahre et al. | |
| 6,939,980 B2 | 9/2005 | Memita et al. | |
| 2003/0118621 A1 | 6/2003 | Heidenfelder et al. | |
| 2004/0258721 A1 | 12/2004 | Bauer et al. | |

FOREIGN PATENT DOCUMENTS

| | | | |
|---|---|---|---|
| EP | 0179416 | * | 10/1984 |
| EP | 0163806 | * | 12/1985 |
| EP | 0 179 416 A2 | | 4/1986 |
| EP | 0301298 | | 2/1989 |
| EP | 1 216 685 A2 | | 6/2002 |
| EP | 1216685 | | 6/2002 |
| EP | 1290999 | | 3/2003 |
| WO | 90/03977 | | 4/1990 |
| WO | WO 96/17591 A1 | | 6/1996 |
| WO | WO 96/17592 A2 | | 6/1996 |
| WO | WO 99/62468 A1 | | 12/1999 |
| WO | 03/028690 | | 4/2003 |

OTHER PUBLICATIONS

Breusch, F.L. et al., Darstellund der di-, tri- and tetra-homologen Reihen der Methan-methylol-fettsaureester, p. 1511-1519, Chem Ber., 1955.*
Lubrajel, Guardian Laboratories, Aug. 4, 2003.*
Gassenmeier, et al., "Sensory Assessment of Lipids in Leave-On and Rinse-Off Products", Chapter 11, Cosmetic Lipids and the Skin Barrier, Edited by Thomas Förster, Marcel Dekker, Inc., New York, (2002), pp. 319-352.
Kosmetikverordnung, Appendix 6, parts A and B.

* cited by examiner

*Primary Examiner* — Bethany Barham
*Assistant Examiner* — Melissa Javier
(74) *Attorney, Agent, or Firm* — Servilla Whitney LLC

(57) ABSTRACT

An oil and water gel composition is provided containing a polymer gel former of a polymer or copolymer of acrylic acid or acrylamide, a wax component having a melting point of at least 30° C. containing esters of pentaerythritol, dipentaerythritol and/or tripentaerythritol, and an oil component liquid at 25° C. and water.

19 Claims, No Drawings

O/W-GEL-COMPOSITIONS HAVING PENTAERYTHRITOL ESTERS OR OLIGOMERS THEREOF

CROSS-REFERENCE TO RELATED APPLICATIONS

This application is filed under 35 U.S.C. §371 claiming priority from Application PCT/EP2005/003232 filed on Mar. 26, 2005, which claims priority from German patent application DE 10 2004 017 221.8 filed on Apr. 5, 2004, the entire contents of each application are incorporated herein by reference.

BACKGROUND OF THE INVENTION

1. Field of the Invention

This invention relates to specific ON/W gel formulations, to their use as skin-care preparations and to a process for their production.

2. Prior Art

Polyacrylate-based gel formulations have long been known to the expert. Many of these gel formulations are surfactant-containing preparations which are used for personal hygiene. Thus, WO 96/17591 and WO 96/17592 describe surfactant-containing skin-cleansing formulations which are stabilized by polymeric gel formers. Although gels impart a sensorially very light and pleasantly cooling sensation, they are not normally used for the formulation of skin-care preparations because their care effects are poor. Polyacrylate-based gel formulations in particular do not have lasting care effects. In addition, gel formulations are salt-sensitive so that, when applied to the skin, they often break through the presence of salts.

BRIEF DESCRIPTION OF THE INVENTION

The problem addressed by the present invention was to provide gel formulations which would have a pleasant, light sensory profile and good care effects and which would not break when applied to the skin. Another problem addressed by the invention was to provide irritation-free formulations.

It has now surprisingly been found that these properties can be achieved by the formulation of o/w gels which contain a combination of certain gel formers, waxes and oils.

Accordingly, the present invention relates to o/w gel compositions containing
(a) 0.05 to 5% by weight of at least one polymeric gel former selected from the group of homopolymers or copolymers of acrylic acid and/or acrylamide and derivatives thereof,
(b) 0.1 to 10% by weight of at least one wax component with a melting point of at least 30° C. selected from the group of pentaerythritol esters, dipentaerythritol esters and/or tripentaerythritol esters,
(c) 1 to 30% by weight of at least one oil component liquid at 25° C. and
(d) 60 to 95% by weight of water.

Compositions of this type are far more stable to the salt content on the skin and, after application, leave the skin feeling smooth and soft with very good care properties. They are easy to apply and spread, are readily absorbed by the skin and leave the skin feeling velvety rather than oily or greasy.

In a preferred embodiment, the compositions according to the invention do not contain any additional anionic and cationic surfactants/emulsifiers. The compositions thus have a low irritation potential.

The o/w gel compositions according to the invention preferably have a viscosity at 20° C. of 50,000 to 500,000 mPa·s, as measured with a Brookfield RVF viscosimeter, spindle TE with Helipath, at 4 r.p.m.

DETAILED DESCRIPTION OF THE INVENTION

Gel Formers

The gel formers are selected from the group of homopolymers or copolymers of acrylic acid and/or acrylamide and derivatives thereof or from a mixture of these substances. The commercially available polymers often also contain a nonionic surfactant/emulsifier. The gel formers suitable for use in accordance with the invention include commercially available substances, such as for example Sepigel® 305, INCI: Polyacrylamide (and) C13-14 Isoparaffin (and) Laureth-7; Sepigel® 501, INCI: Acrylamide Copolymer (and) Mineral oil (and) C13-14 Isoparaffin (and) Polysorbate 85; Sepigel® 502, INCI: C13-14 Isoparaffin (and) Isostearyl Isostearate (and) Sodium Polyacrylate (and) Polyacrylamide (and) Polysorbate 60; Simulgel® 600, INCI: Acrylamide/Sodium Acryloyidimethyltaurate Copolymer (and) Isohexadecane (and) Polysorbate 80; Simulgel® 800, INCI: Sodium Polyacryloyidimethyl Taurate (and) Isohexadecane (and) Sorbitan Oleate; Simulgel® EG, INCI: Sodium Acrylate/Acryloyldimethyl Taurate Copolymer (and) Isohexadecane (and) Polysorbate 80; Simulgel® EG-SL, INCI: Sodium Acrylate/ Acryloyidimethyl Taurate Copolymer (and) Polyisobutene (and) Caprylyl/Capryl Glucoside; Simulgel® NS, INCI: Hydroxyethyl Acrylate (and) Sodium Acryloyldimethyl Taurate Copolymer (and) Squalane (and) Polysorbate 60; Aristoflex® AVC, INCI: Ammonium AcryloyldimethyltaurateNP Copolymer; Aristoflex®) AVC-1, INCI: Ammonium AcryloyldimethyltaurateNinyl Formamide Copolymer; Aristoflex® HMB, INCI: Ammonium Acryloyldimethyltaurate/Beheneth-25-Methacrylate Copolmer; Salcare® SC91, INCI: Sodium Acrylate Copolymer (and) Mineral Oil (and) PPG-1 Trideceth-6; Salcare® AST, INCI: Sodium Acrylate Copolymer (and) Glycine Soya (and) PPG-1 Trideceth-6; Pemulen® TR-1, INCI: Acrylate/10-30 Alkyl Acrylate Crosspolymer; Pemulen® TR-2: Acrylate/C10-30 Alkyl Acrylate Crosspolymer; Carbopol® 980, INCI: Carbomer (for example homopolymers of acrylic acid crosslinked with an allyl ether of pentaerythritol, an allyl ether of sucrose or an allyl ether of propylene); Carbopol® ETD 2020, INCI: Acrylates/C10-30 Alkyl Acrylate Crosspolymer; Carbopol® Ultrez 10, INCI: Carbomer; Rheocare® ATH, INCI: Sodium Polyacrylate (and) Ethylhexyl Stearate (and) Trideceth-6; Rheocare® ATC, INCI: Acrylamide/Sodium Acrylate Copolymer (and) Mineral Oil (and) Trideceth-6.

The polymers may be crosslinked or uncrosslinked. Crosslinked polymers are preferably used. According to the invention, polyacrylates and polyacrylamides are preferred. Polyacrylates and more especially their sodium salts are particularly preferred. According to the invention, a most particularly preferred polymer is commercially available under the name of Cosmedia® SP and Cosmedia® SPL. According to the invention, the polymers are used in quantities of 0.05 to 5% by weight, based on the composition as a whole. Quantities of 0.1 to 4% by weight are preferred, quantities of 0.5 to 3% by weight are particularly preferred and quantities of 0.5 to 2% by weight—based on the composition as a whole—are most particularly preferred.

Wax Components

Waxes are normally understood to be any natural or synthetic substances and mixtures having the following properties: they have a solid to brittle hard consistency, are coarsely to finely crystalline, transparent to opaque and melt above 30° C. without decomposing. Even slightly above their melting point, they are low in viscosity and non-stringing and are very temperature-dependent in their consistency and solubility. A wax component or a mixture of wax components which melt at 30° C. or higher and which are selected from the group of esters of pentaerythritol, dipentaerythritol or tripentaerythritol may be used in accordance with the invention. They are present in the compositions according to the invention in a total quantity of 0.1 to 10% by weight. In a preferred embodiment of the invention, the content of wax component is from 0.2 to 5% by weight, based on the composition as a whole. Quantities of 0.5 to 4% by weight—based on the composition as a whole—are preferred and quantities of 0.5 to 2% by weight particularly preferred. A content of 0.5 to 1.5% by weight of the wax component(s), based on the composition as a whole, is most particularly preferred because the overall sensory profile is optimal in that range. Another preferred embodiment of the o/w gel composition is characterized in that the wax component or mixture of wax components (b) has a melting point of 40° C. to 80° C. and preferably in the range from 40° C. to 60° C. because the best sensory effects are obtained in that range.

In another preferred embodiment of the invention, the wax component (b) is selected from the group of esters of saturated or unsaturated and/or branched or unbranched $C_{6-24}$ fatty acids—preferably $C_{14-22}$ fatty acids—of pentaerythritol, dipentaerythritol and/or tripentaerythritol, less than 0.3% by weight $C_{17}$ fatty acid esters being present. The esters must have a melting point of at least 30° C. They may also be mixed esters, for example of long-chain and short-chain fatty acids, providing they have the required melting point. Another preferred embodiment of the o/w gel composition is characterized in that the wax component (b) is selected from the group of esters which are obtained by reaction of pentaerythritol or dipentaerythritol with a fatty acid mixture containing 40 to 50% by weight $C_{16}$ fatty acid and 45 to 55% by weight $C_{18}$ fatty acid. Esters of linear, unbranched $C_{16/18}$ fatty acids are particularly preferred. Another preferred embodiment of the o/w gel composition contains at least one wax component (b) selected from the groups of esters of pentaerythritol which have a percentage content of (a) 5 to 35% by weight monoesters, (b) 20 to 50% by weight diesters and (c) 25 to 50% by weight triesters and optionally tetraesters. Esters of pentaerythritol which are obtained by reaction of pentaerythritol with a fatty acid mixture containing 40 to 50% by weight $C_{16}$ fatty acid and 45 to 55% by weight $C_{18}$ fatty acid and which have the following ester distribution: (a) 12 to 19% by weight monoesters, (b) 25 to 35% by weight diesters and (c) 30 to 40% by weight triesters and 6 to 11% by weight tetraesters, are most particularly preferred.

Oil Components

The o/w gels according to the invention contain 1 to 30% by weight, based on the composition as a whole, of an oil component liquid at 25° C. or a mixture of such oil components. The oil component(s) is/are present in a total quantity of 3 to 20% by weight, preferably in a quantity of 5 to 15% by weight and more particularly in a quantity of 7 to 12% by weight. Suitable oil components are, for example, the classes of compounds mentioned in the following, providing they are liquid at 25° C. These include inter alia Guerbet alcohols based on fatty alcohols containing 6 to 18 and preferably 8 to 10 carbon atoms, esters of linear or branched, saturated or unsaturated $C_{6-22}$ fatty acids with linear or branched, saturated or unsaturated $C_{6-22}$ fatty alcohols, more particularly 2-ethyl hexanol. The following are mentioned by way of example: hexyl laurate, myristyl isostearate, myristyl oleate, cetyl isostearate, cetyl oleate, stearyl isostearate, stearyl oleate, isostearyl myristate, isostearyl palmitate, isostearyl stearate, isostearyl isostearate, isostearyl oleate, oleyl myristate, oleyl isostearate, oleyl oleate, oleyl erucate, erucyl isostearate, erucyl oleate, cococaprylate/caprate. Other suitable esters are, for example, esters of $C_{18-38}$ alkylhydroxycarboxylic acids with linear or branched, saturated or unsaturated $C_{6-22}$ fatty alcohols, esters of linear and/or branched, saturated and/or unsaturated fatty acids with polyhydric alcohols (for example propylene glycol, dimer diol or trimer triol) and/or Guerbet alcohols, triglycerides or triglyceride mixtures, mono-, di- and triglyceride mixtures, esters of $C_{6-22}$ fatty alcohols and/or Guerbet alcohols with aromatic carboxylic acids, more particularly benzoic acid, esters of $C_{2-12}$ dicarboxylic acids with linear or branched, saturated or unsaturated alcohols containing 1 to 22 carbon atoms or polyols containing 2 to 10 carbon atoms and 2 to 6 hydroxyl groups, vegetable oils, branched primary alcohols, substituted cyclohexanes, linear dialkyl carbonates, Guerbet carbonates based on fatty alcohols containing 6 to 18 and preferably 8 to 10 carbon atoms, esters of benzoic acid with linear and/or branched $C_{6-22}$ alcohols (for example Cetiol® AB), linear or branched, symmetrical or non-symmetrical dialkyl ethers containing 6 to 22 carbon atoms per alkyl group such as, for example, Di-n-octyl Ether (Cetiol® OE) or ring opening products of epoxidized fatty acid esters with polyols, hydrocarbons, such as paraffin or mineral oils, silicone oils and oligo- or poly-α-olefins.

According to the invention, dialkyl carbonates and esters of $C_{8-24}$ faty acids and $C_{8-24}$ fatty alcohols or mixtures thereof are preferred oil components. The dialkyl carbonates may be symmetrical or asymmetrical, branched or unbranched, saturated or unsaturated and may be produced by transesterification reactions known from the prior art. According to the invention, dialkyl carbonates with alkyl chains containing 6 to 24 carbon atoms, more particularly di-n-octyl carbonate or di-(2-ethylhexyl) carbonate, or mixtures thereof are particularly suitable. Of these, di-n-octyl carbonate is preferred.

The hydrocarbons suitable for use in accordance with the invention have a chain length of 8 to 40 carbon atoms. They may be branched or unbranched, saturated or unsaturated. Of these, branched, saturated $C_{8-40}$ alkanes are preferred. Both pure substances and mixtures may be used. The mixtures are normally mixtures of different isomeric compounds. Compositions containing $C_{10-30}$, preferably $C_{12-20}$ and more particularly $C_{16-20}$ alkanes are particularly suitable and, of these, a mixture of alkanes containing at least 10% by weight branched alkanes, based on the total quantity of alkanes, is particularly preferred. The alkanes are preferably branched, saturated alkanes. Mixtures of alkanes containing more than 1% by weight 5,8-diethyl dodecane and/or more than 1% by weight didecene are particularly suitable.

A preferred embodiment of the o/w gel composition according to the invention contains (a) 0.05 to 5% by weight of at least one polyacrylate, (b) 0.1 to 10% by weight of at least one $C_{16/18}$ ester of pentaerythritol and/or dipentaerythritol, (c) 1 to 30% by weight of at least one oil component and (d) 60 to 95% by weight water. The polyacrylate (a) is preferably a sodium polyacrylate. The oil components are preferably selected from the fatty acid esters or dialkyl carbonates or mixtures thereof.

Another preferred embodiment is an o/w gel composition containing (a) 0.5 to 2% by weight of at least one sodium polyacrylate, (b) 0.5 to 2.0% by weight of at least one ester obtained by reaction of pentaerythritol and/or dipentaerythritol with a fatty acid mixture containing 40 to 50% by weight $C_{16}$ fatty acid and 45 to 55% by weight $C_{18}$ fatty acid, (c) 7 to 12% by weight of at least one oil component selected from fatty acid esters, triglycerides, dialkyl carbonates, hydrocarbons, dialkyl ethers liquid at 25° C. or mixtures thereof and (d) 60 to 95% by weight water. The esters (b) are preferably pentaerythritol esters with the following ester distribution: 12 to 19% by weight monoesters, 25 to 35% by weight diestersm 30 to 40% by weight triesters and 6 to 11% by weight tetraesters.

The present invention also relates to a process for the production of the o/w gel composition according to the invention in which either a) the gel former or a mixture of the gel formers (a) is dispersed in the liquid oil phase containing the wax and oil components and the resulting dispersion is subsequently emulsified with the aqueous phase or b) the gel former or a mixture of the gel formers is swollen in the aqueous phase and the whole is mixed with the liquid oil phase or c) the gel former or a mixture of the gel formers is swollen in a low molecular weight polyol or polyol mixture with a molecular weight of <1,000 dalton and the whole is processed with the aqueous phase and with the liquid oil phase.

The present invention also relates to the use of the o/w gel composition according to the invention for body care. The present invention also relates to the use of esters of pentaerythritol, dipentaerythritol and/or tripentaerythritol for improving the salt tolerance of the gel compositions claimed in claim 1.

Other Optional Auxiliaries and Additives

Depending on their intended application, the cosmetic formulations contain a number of other auxiliaries and additives such as, for example, emulsifiers/surfactants, other wax or lipid components, other thickeners, superfatting agents, stabilizers, polymers, lecithins, phospholipids, biogenic agents, UV protection factors, antioxidants, deodorants, film formers, swelling agents, insect repellents, hydrotropes, solubilizers, preservatives. perfume oils, dyes, etc. which are listed by way of example in the following. The quantities in which the particular additives are used is determined by the intended use.

According to the invention, fats and fat-like substances with a wax-like consistency may be used as other waxes/lipid components. These include inter alia fats (triglycerides), mono- and diglycerides, natural and synthetic waxes, fatty and wax alcohols, fatty acids, esters of fatty alcohols and fatty acids and also fatty acid amides or mixtures of these substances.

Fats in the context of the invention are understood to be triacylglycerols, i.e. the triple esters of fatty acids with glycerol. They preferably contain saturated, unbranched and unsubstituted fatty acid components. They may also be mixed esters, i.e. triple esters of glycerol with various fatty acids. So-called hardened fats and oils obtained by partial hydrogenation may be used in accordance with the invention and are particularly suitable as consistency factors. Vegetable hardened fats and oils, for example hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, are preferred.

Suitable fats are inter alia the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the name of Cutina® HR. Gycerol tristearate, glycerol tribehenate (for example Syncrowax® HRC), glycerol tripalmitate or the triglyceride mixtures known under the name of Syncrowax® HGLC are also suitable.

According to the invention, suitable additional wax components are, in particular, mono- and diglycerides and mixtures of these partial glycerides. Glyceride mixtures suitable for use in accordance with the invention include the products Novata® AB and Novata® B (mixture of $C_{12-18}$ mono-, di- and triglycerides) and Cutina® MD or Cutina® GMS (glyceryl stearate) marketed by Cognis Deutschland GmbH & Co. KG.

Mixed esters and mixtures of mono-, di- and triglycerides are particularly suitable for the purposes of the invention because they have a relatively low tendency towards crystallization and thus improve the performance of the composition according to the invention.

Fatty alcohols suitable for use in accordance with the invention include $C_{12-50}$ fatty alcohols and, more particularly, $C_{12-24}$ fatty alcohols obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, saturated, unbranched fatty alcohols are preferred. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols®) or the partly branched alcohols from the oxosynthesis (Dobanols®) may also be used. The $C_{14-18}$ fatty alcohols marketed, for example, by Cognis Deutschland GmbH under the name of Lanette® 16 ($C_{16}$ alcohol), Lanette® 14 ($C_{14}$ alcohol), Lanette® O ($C_{16/18}$ alcohol) and Lanette® 22 ($C_{18/22}$ alcohol) are particularly suitable for the purposes of the invention. Fatty alcohols give the compositions a dryer feeling on the skin than triglycerides and are therefore preferred to triglycerides.

$C_{14-40}$ fatty acids or mixtures thereof may also be used as additional wax components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes suitable for use in accordance with the present invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The additional wax component may also be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols, from the group of polyols esterified with carboxylic acids (other than pentaerythritol, dipentaerythritol or tripentaerythritol) and also from the group of lactides of long-chain hydroxycarboxylic acids. Examples of such esters are the $C_{16-40}$ alkyl stearates, $C_{20-40}$ alkyl stearates (for example Kesterwachs® K82H), $C_{20-40}$ dialkyl esters of dimer acids, $C_{18-38}$ alkyl hydroxystearoyl stearates or $C_{20-40}$ alkyl erucates. $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetearyl behenate and behenyl behenate may also be used.

Anionic, nonionic, cationic and/or amphoteric or zwitterionic surfactants/emulsifiers or a mixture of these surfactants/emulsifiers may also be present as surfactants. The surfactant content depends on the nature of the formulation, but does not normally exceed 10% by weight. A preferred embodiment of the invention does not contain any anionic or cationic surfactants, but does contain nonionic surfactants. The nonionic surfactants may also be present inter alia in the commercially available gel formers. The preferred nonionic surfactant content is between 0 and 5% by weight and more particularly between 0.1 and 3% by weight, based on the overall composition of the gel.

Typical examples of anionic surfactants are soaps, alkyl benzene-sulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol esters, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Other suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, polyvinyl alcohol, polyvinyl pyrrolidone and bentonites such as, for example, Bentone® GelVS-5PC (Rheox).

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. Typical UV-A filters are, in particular, derivatives of benzoyl methane. The UV-A and UV-B filters may of course also be used in the form of mixtures, for example combinations of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene), and esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are often combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorizing components counteract, mask or eliminate body odors. Body odors are formed through the action of skin bacteria on apocrine perspiration which results in the formation of unpleasant-smelling degradation products. Accordingly, suitable deodorizing components are inter alia germ inhibitors, enzyme inhibitors, odor absorbers or odor maskers.

Suitable insect repellents are, for example, N,N-diethyl-m-toluamide, pentane-1,2-diol or 3-(N-n-butyl-N-acetylamino)-propionic acid ethyl ester), which is marketed as Insect Repellent® 3535 by Merck KGaA, and Butylacetylaminopropionate.

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

In addition, hydrotropes, such as for example ethanol, isopropyl alcohol or polyols, may be used to improve flow behavior. Suitable polyols preferably contain 2 to 15 carbon atoms and at least two hydroxyl groups.

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Suitable perfume oils are mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, and synthetic perfume compounds of the ester, ether, aldehyde, ketone, alcohol and hydrocarbon type, are also suitable.

Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

EXAMPLES

The quantities shown in the following Table represent % by weight of the commercially available substance, based on the composition as a whole.

| Ingredient Commercial name/INCI | C1 | C2 | C3 | 1 | 2 | 3 | 4 | 5 |
|---|---|---|---|---|---|---|---|---|
| Cosmedia ® SP Sodium polyacrylate | 1.0 | | 1.0 | 1.0 | 1.0 | 1.0 | 1.0 | |
| Sepigel ® 305 Polyacrylamide (and) C13-14 Isoparaffin (and) Laureth-7 | | 0.3 | | | | | | 0.3 |
| Pentaerythrityl Disearate[1] | | | | 1.0 | 1.0 | 2.0 | 1.0 | 1.0 |
| Dow Corning ® 245 Cyclomethicone | | | | | | | | |
| Ethanol | | | | | | | 15.0 | |
| Sodium chloride | | | 0.5 | 0.5 | | | | |
| Cetiol ® CC Dicaprylyl Carbonate | 5.0 | 5.0 | 5.0 | 5.0 | 5.0 | 5.0 | 5.0 | 5.0 |
| Cetiol ® LC Coco-Caprylate/Caprate | 5.0 | 5.0 | 5.0 | 5.0 | 5.0 | 5.0 | 5.0 | 5.0 |
| Water | to 100 | to 100 | to 100 | to 100 | to 100 | to 100 | to 100 | to 100 |
| Viscosity at 20° C. after 1 week | 125000 | 37500 | — | 5200 | 162500 | 187500 | 12500 | 50000 |
| Phase stability at −5° C./20° C./40° C. | | | | | | | | |
| After 1 week | 1/1/1 | 1/1/1 | 5/5/5 | 1/1/1 | 1/1/1 | 1/1/1 | 1/1/1 | 1/1/1 |
| After 4 weeks | 1/1/1 | | 5/5/5 | | 1/1/1 | 1/1/1 | 1/1/1 | |
| After 12 weeks | 1/1/1 | | 5/5/5 | | 1/1/1 | 1/1/1 | | |
| Sensory evaluation | | | | | | | | |
| Smoothness | − | − | − | | ++ | + | ++ | ++ |
| Softness | − | − | − | | ++ | + | ++ | + |
| Acceptance | − | − | − | | ++ | + | ++ | + |

[1]The Pentaerythrityl Distearate is an ester mixture which is obtained by reaction of pentaerythritol with a fatty acid mixture containing 42 to 48% by weight C16 fatty acid and 50 to 56% by weight C18 fatty acid (rest: ≤C14 fatty acids and >C18 fatty acids), has the following ester distribution: 12 to 19% by weight monoesters, (b) 25 to 35% by weight diesters, (c) 30 to 40% by weight triesters and (d) 6 to 11% by weight tetraesters, and contains less than 0.3% by weight $C_{17}$ fatty acid acyl groups.

Viscosity Measurement
  In C1, C2 and Examples 2 to 6: 20° C., Brookfield RVF viscosimeter, spindle TE with Helipath, 4 r.p.m.
  In C3 and Example 1: 23° C., Brookfield RVF viscosimeter, spindle 5, 10 r.p.m.
Visual Evaluation of Phase Stability
1=stable; 2=very slight separation; 3=slight separation; 4=distinct separation; 5=complete separated
Sensory Evaluation
++=excellent; +=very good; 0=good, −=medium; −−=unsatisfactory
Test group: 10 experienced and trained volunteers
  10 μl of the above compositions brought beforehand to 20° C. were applied by micropipette to the hair-free side of the forearm of the volunteers and rubbed in with the fingers of the hands of the contralateral side. The sensory profile was evaluated during and after absorption.

The sensory test was conducted on 10 volunteers, as described in the book "Cosmetic Lipids and the Skin Barrier" (Marcel Dekker, New York, 2002; Ed.: Thomas Förster, pp. 319-352).

We claim:
1. An O/W gel composition containing:
  (a) 0.05 to 5% by weight of at least one polymeric gel former selected from the group consisting of homopolymers of acrylic acid, copolymers of acrylic acid, homopolymers of acrylamide, copolymers of acrylamide and derivatives thereof,
  (b) 0.1 to 10% by weight of at least one wax component with a melting point of at least 30° C. comprising a mixture of pentaerythritol esters, said mixture compris- ing at least two pentaerythritol esters selected from the group consisting of monoesters, diesters, triesters, and tetraesters, wherein 5 to 35% by weight of said pentaerythritol esters are monoesters and said mixture comprising at least one pentaerythritol fatty acid ester in which the fatty acid portion comprises saturated or unsaturated, branched or unbranched C16-18 fatty acids and in which the pentaerythritol portion comprises at least one pentaerythritol selected from the group consisting of monopentaerythritol, dipentaerythritol and tripentaerythritol, wherein, less than 0.3% by weight of C17 fatty acid ester groups are present based on the total weight of said mixture, (c) 1 to 30% by weight of at least one oil component liquid at 25° C. and (d) 60 to 95% by weight of water.

2. The O/W gel composition as claimed in claim 1, wherein, the composition does not contain any anionic or cationic emulsifiers/surfactants.

3. The O/W gel composition as claimed in claim 1, wherein, the wax component (b) is present in a quantity of 0.2 to 5% by weight, based on the composition as a whole.

4. The O/W gel composition as claimed in claim claim 1, wherein, the wax component (b) comprises a mixture of pentaerythritol esters, said mixture comprising at least one pentaerythritol ester selected from the group consisting of monopentaerythritol esters and dipentaerythritol esters containing 40 to 50% by weight C16 fatty acid residues and 45 to 55% by weight C18 fatty acid residues.

5. The O/W gel composition as claimed in claim 4, wherein, the wax component (b), comprises, a mixture of esters of pentaerythritol with a content of (a) 5 to 35% by weight monoesters, (b) 20 to 50% by weight diesters and (c) 25 to 50% by weight triesters and optionally tetraesters.

6. The O/W gel composition as claimed in claim 1 containing:
(a) 0.05 to 5% by weight of at least one polyacrylate,
(b) 0.1 to 10% by weight of said mixture of at least two pentaerythritol esters, wherein said mixture comprises at least one pentaerythritol ester selected from the group consisting of $C_{16/18}$ esters of monopentaerythritol and $C_{16/18}$ esters of dipentaerythritol,
(c) 1 to 30% by weight of at least one oil component and
(d) 60 to 95% by weight water.

7. The O/W gel composition as claimed in claim 6, wherein, the polyacrylate (a) is a sodium polyacrylate.

8. The O/W gel composition as claimed in claim 6, wherein, the oil component comprises at least one member selected from the group consisting of fatty acid esters and dialkyl carbonates.

9. The O/W gel composition as claimed in claim 1, wherein, the composition has a viscosity at 20° C. of 50,000 to 500,000 mPas, as measured with a Brookfield RVF viscosimeter, spindle TE with Helipath, at 4 r.p.m.

10. The O/W gel composition as claimed in claim 2, wherein, the wax component (b) is present in a quantity of 0.2 to 5% by weight, based on the composition as a whole.

11. The O/W gel composition as claimed in claim 2 containing:
(a) 0.05 to 5% by eight of at least one polyacrylate,
(b) 0.1 to 10% by weight of said mixture of at least two pentaerythritol esters, wherein said mixture comprises at least one pentaerythritol ester selected from the group consisting of $C_{16/18}$ esters of monopentaerythritol and $C_{16/18}$ esters of dipentaerythritol,
(c) 1 to 30% by weight of at least one oil component and
(d) 60 to 95% by weight water.

12. The O/W gel composition as claimed in claim 2, wherein, the composition has a viscosity at 20° C. of 50,000 to 500,000 mPas, as measured with a Brookfield RVF viscosimeter, spindle TE with Helipath, at 4 r.p.m.

13. The O/W composition as claimed in claim 2, wherein, the polyacrylate (a) comprises a sodium polyacrylate.

14. The O/W gel composition as claimed in claim 1, wherein the wax component (b) comprises a mixture of pentaerythritol esters in which the pentaerythritol portion comprises at least one member selected from the group consisting of monopentaerythritol, dipentaerythritol, and tripentaerythritol.

15. The O/W gel composition as claimed in claim 4, wherein, the wax component (b), comprises, a mixture of esters of pentaerythritol with a content of (a) 12 to 19% by weight monoesters, (b) 25 to 35% by weight diesters, (c) 30 to 40% by weight triesters, and 6 to 11% by weight tetraesters.

16. A process for the production of an O/W gel composition as claimed in claim 1, wherein, the process is selected from the group consisting of (1) dispersing the gel former or a mixture of the gel formers (a) in the liquid oil phase containing the wax and oil components and emulsifying the resulting dispersion with the aqueous phase, (2) swelling the gel former or mixture of gel formers in the aqueous phase to form a mixture of swollen gel former and aqueous phase and emulsifying the mixture with the liquid oil phase and wax, and (3) swelling the gel former or mixture of gel formers in a low molecular weight polyol or mixture of polyols with a molecular weight of <1,000 dalton, to form a mixture of swollen gel former and polyol, and emulsifying the mixture with the aqueous phase, the liquid oil phase and wax.

17. A body care composition comprising the O/W gel composition claimed in claim 1.

18. An O/W gel composition with improved salt tolerance comprising a polymer gel former, an oil, water and a salt tolerance improving amount of esters of pentaerythritol, dipentaerythritol and of at least one member selected from the group consisting of tripentaerythritol, whereby, the salt tolerance of gel compositions containing the gel formers claimed in claim 1 is improved.

19. An O/W gel composition with improved salt tolerance comprising a polymer gel former, an oil, water and a salt tolerance improving amount of esters of at least one member selected from the group consisting of monopentaerythritol, dipentaerythritol and tripentaerythritol, whereby, the salt tolerance of gel compositions containing the gel formers claimed in claim 2 is improved.

* * * * *